United States Patent [19]

Eicken et al.

[11] Patent Number: 5,442,073
[45] Date of Patent: Aug. 15, 1995

[54] PREPARATION OF ALKYL 2-ALKYL-4-FLUOROMETHYL-THIAZOLECARBOXYLATES

[75] Inventors: Karl Eicken, Wachenheim; Klaus Ditrich, Bad Duerkheim; Thomas Mueller, Hessheim; Oliver Wagner, Bexbach, all of Germany

[73] Assignee: BASF Aktiengesellscahft, Ludwigshafen, Germany

[21] Appl. No.: 182,701

[22] Filed: Jan. 13, 1994

[30] Foreign Application Priority Data

Jan. 20, 1993 [DE] Germany .................. 43 01 356.2

[51] Int. Cl.⁶ .............................................. C07D 277/56
[52] U.S. Cl. .................................................. 548/201
[58] Field of Search ....................................... 548/201

[56] References Cited

FOREIGN PATENT DOCUMENTS 276177 7/1988 European Pat. Off. .
371950 6/1990 European Pat. Off. .

OTHER PUBLICATIONS

Metzger Thiazole & Its Derivatives, v 34 pt 1 pp. 188–191 (1979).

*Primary Examiner*—Robert Gerstl
*Attorney, Agent, or Firm*—Keil & Weinkauf

[57] ABSTRACT

A process for preparing alkyl 2-alkyl-4-fluoromethyl-thiazolecarboxylates of the formula I

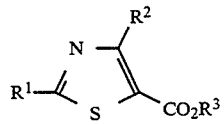

where
$R^1$ is alkyl,
$R^2$ is difluoromethyl or trifluoromethyl and
$R^3$ is alkyl,
by reacting thiocarboxamides of the formula II

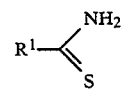

where $R^1$ has the abovementioned meaning, with alkyl 2-chloro-4-fluoroacetoacetamides of the formula III

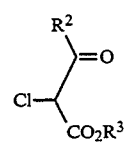

where $R^2$ and $R^3$ have the abovementioned meanings, in an aprotic solvent at below 100° C. and reacting with a dehydrating agent, in the presence of a base, at below 80° C. is described.

8 Claims, No Drawings

PREPARATION OF ALKYL 2-ALKYL-4-FLUOROMETHYLTHIAZOLECARBOXYLATES

The invention relates to a process for preparing alkyl 2-alkyl-4-fluoromethylthiazolecarboxylates.

It has been disclosed to react thioacetamide with ethyl 2-chloro-4,4,4-trifluoromethylacetate with relatively slow heating to above 110° C. in dimethylformamide or glacial acetic acid, ethyl 2-methyl-4-trifluoromethylthiazolecarboxylate being obtained in modest yields (38% or 56%) after purification by distillation or column chromatography (EP 276 177, 371 950).

It has now been found that alkyl 2-alkyl-4-fluoromethylthiazolecarboxylates of the formula I

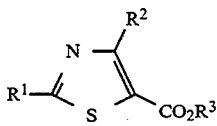

where
$R^1$ is $C_1$–$C_4$-alkyl,
$R^2$ is difluoromethyl or trifluoromethyl and
$R^3$ is $C_1$–$C_6$-alkyl,
are obtained in very good yields if thiocarboxamides of the formula II

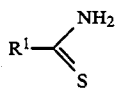

where $R^1$ has the abovementioned meaning, are reacted with alkyl 2-chloro-4-fluoroacetoacetates of the formula III

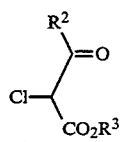

where $R^2$ and $R^3$ have the abovementioned meanings, in an aprotic solvent at below 100° C. and the product is reacted with a dehydrating agent, in the presence of a base, at below 80° C.

The alkyl radicals are specifically eg. the following
$R^1$ is methyl, ethyl, n-propyl, i-propyl, n-butyl, sec-butyl, i-butyl,
$R^3$ is methyl, ethyl, n-propyl, i-propyl, n-butyl, sec-butyl, i-butyl, n-pentyl, n-hexyl.

A preferred starting material of the formula II is thioacetamide.

Preferred starting materials of the formula III are methyl or ethyl 2-chloro-4,4,4-trifluoroacetoacetates or methyl or ethyl 2-chloro-4,4-difluoroacetoacetates.

Suitable aprotic solvents are:
N,N-dialkylamides, eg. N,N-dimethylformamide, N,N-diethylformamide, N,N-dimethylacetamide,
cyclic ureas, eg. N,N'-dimethylethyleneurea, N,N'-dimethylpropyleneurea,
lactams, eg. N-methylpyrrolidone, N-methylpiperidone,
nitriles, eg. acetonitrile, propionitrile, benzonitrile,
halogenated hydrocarbons which are inert under the reaction conditions, eg. dichloromethane, chloroform,
ketones, eg. acetone, methyl ethyl ketone, methyl isobutyl ketone,
ethers, eg. 1,2-dimethoxyethane, tetrahydrofuran, dioxane
or mixtures of these compounds.

Suitable dehydrating agents are eg.
anhydrides, eg. acetic anhydride, trichloroacetic anhydride, chloroacetic anhydride, trifluoroacetic anhydride, perfluorobutyric anhydride,
carbonyl chlorides, eg. acetyl chloride, trichloroacetyl chloride,
chloro derivatives of carbonic acid such as eg. phosgene, trichloromethyl chlorocarbonate, methyl or ethyl chlorocarbonate,
sulfonyl chlorides, eg. methanesulfonyl chloride, trichloromethylsulfonyl chloride, trifluoromethylsulfonyl chloride, benzenesulfonyl chloride, tosyl chloride,
chloro compounds of sulfurous acid, sulfuric acid, phosphorous acid or phosphoric acid, eg. thionyl chloride, sulfuryl chloride, chlorosulfonic acid, phosphorus trichloride, phosphorus oxychloride.

The use of nitriles, eg. acetonitrile, as a solvent or as a constituent of solvent mixtures is advantageous, in particular in combination with chloro compounds of sulfurous acid or sulfuric acid.

Suitable bases are in general organic bases, eg. tertiary amines, eg. trimethylamine, triethylamine, diisopropylethylamine, tri-n-butylamine, N,N-dimethylcyclohexylamine, N-methylpyrrolidine, N-methylpiperidine, diazabicyclo[2.2.2]octane, pyridines such as pyridine, picolines, collidine, quinoline.

Inorganic bases, eg. alkali metal carbonates, alkali metal bicarbonates or alkali metal or alkaline earth metal hydroxides, can also be used. In these cases, drying of the aprotic solvent must be carried out before addition of the organic base and of the dehydrating agent.

The starting materials of the formulae II and III are preferably employed in stoichiometric amounts or in a small excess. The dehydrating agent is used in at least equimolar amounts, in particular in an equimolar amount or 1–10% molar excess.

In relation to the starting materials, the organic bases are employed in at least two to three times the molar amounts, depending on the type of dehydrating agent, where combinations of two bases which differ in their basicity can be expedient. If an inorganic base is used for bonding of the chlorohydrocarbon formed from the reactants of the formulae II and III, the amount of organic base is unavoidably reduced by an amount equimolar to the inorganic base during the treatment with the dehydrating agent.

The temperatures in the reaction of the compounds of the formulae II and III are below 100° C., in particular −30° C.-70° C., preferably 0° C.-40° C. If the dehydrating agent is used, the temperatures are in the same range, but to accelerate the dehydration it can be advantageous to carry the reaction to completion above 0° C., depending on the type of dehydrating agent used.

The reaction mixture is worked up eg. by diluting with water and extracting the thiazolecarboxylate formed with solvents which are immiscible with water, such as eg. hexane, cyclohexene, toluene, ethers such as methyl tert-butyl ether, dichloromethane or mixtures of these compounds.

When using an aprotic water-miscible solvent for carrying out the reaction, it is advantageous to evaporate this solvent after completion of the reaction and then to proceed as described above.

When using a small excess of dehydrating agent, it is advantageous after the extraction of the thiazolecarboxylate to add a washing of the extraction liquid, which contains the thiazolecarboxylate, with dilute alkalis eg. sodium bicarbonate solution to remove acidic constituents. The thiazolecarboxylates of the formula I obtained after evaporating the extracting agent is usually very pure and can be further processed immediately, eg. by alkaline hydrolysis to give the corresponding acid.

EXAMPLE 1

43.7 g of ethyl 2-chloro-4,4,4-trifluoroacetoacetate are added dropwise at 20°–25° C. to a solution of 15.0 g of thioacetamide in 200 ml of acetonitrile. After stirring at room temperature (20° C.) for 12 hours the mixture is cooled to 0° C.–5° C., a mixture of 20.2 g of triethylamine and 44.6 g of 2-picoline is added dropwise, the mixture is stirred for 15 minutes, then 44.1 g of trifluoroacetic anhydride are added dropwise and the mixture is stirred at room temperature for 1 hour. After evaporation of the solvent in vacuo (20 mbar, 35° C.), the residue is partitioned between 200 ml of methyl tert-butyl ether and 200 ml of 2N hydrochloric acid. After washing the organic phase with 200 ml of water, 100 ml of sodium bicarbonate solution, drying and evaporating the solvent, 45.4 g (95%) of ethyl 2-methyl-4-trifluoromethylthiazolecarboxylate are isolated. HPLC purity (high pressure liquid chromatography) (acetonitrile/water 7:3) 90%.

EXAMPLE 2

8.7 g of ethyl 2-chloro-4,4,4-trifluoroacetoacetate are added dropwise at 5° C. to a solution of 3.0 g of thioacetamide in 40 ml of acetonitrile. After stirring at room temperature (20° C.) for 12 hours, the mixture is cooled to 5° C., a mixture of 8.9 g of triethylamine and 4.8 g of 2-picoline is added dropwise, the mixture is stirred for a further 10 minutes and 5.3 g of methanesulfonyl chloride are then added dropwise and the mixture is stirred at room temperature for a further 6 hours. After evaporating the solvent, the residue is partitioned between 40 ml of methyl tertbutyl ether and 40 ml of 2N hydrochloric acid. After washing the organic phase with 40 ml of sodium bicarbonate solution, drying and evaporating the solvent, 8.7 g (91%) of ethyl 2-methyl-4-trifluoromethylthiazolecarboxylate are isolated. HPLC purity (acetonitrile/water 7:3) 96.4%.

EXAMPLE 3

47.0 g of ethyl 2-chloro-4,4,4-trifluoroacetoacetate are added dropwise at 5° C.–10° C. to a solution of 16.1 g of thioacetamide in 180 ml of acetonitrile. After stirring at room temperature for 10 hours, the mixture is cooled to 3°–7° C., 71.6 g of triethylamine and then 28.1 g of thionyl chloride are added dropwise and it is stirred for a further hour at room temperature. After evaporating the solvent, the residue is partitioned between 200 ml of water and 100 ml of methyl tert-butyl ether. After extracting the aqueous phase with 100 ml of methyl tert-butyl ether, the combined organic phases are washed with 20 ml of water. After drying and evaporating the solvent, 48.7 g (94.7%) of ethyl 2-methyl-4-trifluoromethylthiazolecarboxylate are obtained. HPLC purity (acetonitrile/water 7:3) 98%.

We claim:

1. A process for preparing alkyl 2-alkyl-4-fluoromethylthiazolecarboxylates of the formula I

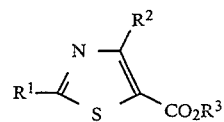

where
$R^1$ is $C_1$–$C_4$-alkyl,
$R^2$ is difluoromethyl or trifluoromethyl and
$R^3$ is $C_1$–$C_6$-alkyl,
which comprises reacting alkyl 2-chloroacetoacetates, substituted in the 4-position by fluorine, of the formula III

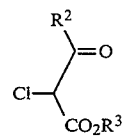

where $R^2$ and $R^3$ have the abovementioned meanings, with thiocarboxamides of the formula II

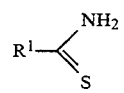

where $R^1$ has the abovementioned meaning, in an aprotic solvent at below 100° C. and reacting with a dehydrating agent, in the presence of a base, at below 80° C.

2. A process for preparing alkyl 2-methyl-4-trifluoromethylthiazolecarboxylates as defined in claim 1, wherein an alkyl 2-chloro-4,4,4-trifluoroacetoacetate is reacted with thioacetamide.

3. A process for preparing alkyl 2-methyl-4-difluoromethylthiazolecarboxylates as defined in claim 1, wherein an alkyl 2-chloro-4,4-difluoroacetoacetate is reacted with thioacetamide.

4. The process as defined in claim 1, wherein the reaction of the compounds II and III is carried out at from 0° to 40° C.

5. The process as defined in claim 1, wherein the reaction with the dehydrating agent is carried out at from 0° to 40° C.

6. The process as defined in claim 1, wherein the compound of the formula II used is thioacetamide.

7. The process as defined in claim 1, wherein the compound of the formula III used is ethyl 2-chloro-4,4,4-trifluoroacetoacetate.

8. The process as defined in claim 1, wherein the aprotic solvent used is acetonitrile or acetonitrile-containing solvent mixtures.

* * * * *